(12) United States Patent
Shoenman et al.

(10) Patent No.: US 6,755,825 B2
(45) Date of Patent: *Jun. 29, 2004

(54) ELECTROSURGICAL DEVICE HAVING A DIELECTRIC SEAL

(75) Inventors: Arthur Shoenman, Longmont, CO (US); Joe D. Sartor, Longmont, CO (US); Vernita Kelm, Lafayette, CO (US)

(73) Assignee: Sherwood Services AG, Schaffhausen (CH)

( * ) Notice: Subject to any disclaimer, the term of this patent is extended or adjusted under 35 U.S.C. 154(b) by 246 days.

This patent is subject to a terminal disclaimer.

(21) Appl. No.: 09/951,592

(22) Filed: Sep. 13, 2001

(65) Prior Publication Data

US 2002/0035364 A1 Mar. 21, 2002

Related U.S. Application Data

(62) Division of application No. 09/396,897, filed on Sep. 15, 1999.
(60) Provisional application No. 60/105,367, filed on Oct. 23, 1999.

(51) Int. Cl.$^7$ ............................................. A61B 18/18
(52) U.S. Cl. ......................................... 606/45; 606/49
(58) Field of Search ............................. 606/34, 41, 42, 606/45, 48, 49, 50; 604/21, 22, 35

(56) References Cited

U.S. PATENT DOCUMENTS

| | | | |
|---|---|---|---|
| 3,421,509 A | 1/1969 | Fiore | |
| 3,565,078 A | 2/1971 | Vailliancourt et al. | |

(List continued on next page.)

FOREIGN PATENT DOCUMENTS

| | | |
|---|---|---|
| DE | 3217118 | 8/1983 |
| DE | 3802853 | 1/1989 |

(List continued on next page.)

*Primary Examiner*—Rosiland Rollins

(57) ABSTRACT

An electrosurgical device is provided having at least one elastomeric seal capable of providing bio-contamination and dielectric protection by inhibiting the ingress of fluids and contaminants through the nose and actuator areas. The elastomeric seal is manufactured from a thermoplastic elastomer or resin which while in liquid form is placed within a mold. A housing section having the main circuit components and mechanisms of the electrosurgical device is then placed within the mold. Once the elastomer cures, the elastomeric seal seals the components and mechanisms within the housing partial-section. The elastomeric seal defines a flexible first opening at a distal end of the electrosurgical device to accommodate varying diameters of electrodes or blades connected to the nose area of the electrosurgical device. An actuator seal is also provided on the actuator area of the electrosurgical device to prevent fluids and contaminants from entering the electrosurgical device through the actuator area. Two buttons are insert molded within the actuator seal and are operatively associated with a self-cleaning switching mechanism within the housing section to operate the electrosurgical device between a cutting and coagulating mode. The actuator seal is also manufactured from a thermoplastic elastomer or resin. The self-cleaning switching mechanism includes a switch contact plate having pair of movable contacts having contact faces. Each movable contact corresponds to a stationary contact positioned within a circuit mold. As the actuator seal is depressed, contact faces of the movable and stationary contacts slide along each other to clean the contacts from non-conductive corrosion and contaminants. The device is further provided with a plug connector having a counting mechanism for counting the number of times the device is plugged into an electric generator. A disable mechanism is included at the proximal end of the plug connector to disable the device after a pre-determined number of operations.

9 Claims, 16 Drawing Sheets

U.S. PATENT DOCUMENTS

| | | |
|---|---|---|
| 3,648,001 A | 3/1972 | Anderson et al. |
| 3,801,766 A | 4/1974 | Morrison, Jr. |
| 3,853,127 A | 12/1974 | Spademan |
| 3,907,310 A | 9/1975 | Dufour |
| 3,911,241 A | 10/1975 | Jarrard |
| 3,994,287 A | 11/1976 | Turp et al. |
| 4,000,739 A | 1/1977 | Stevens |
| 4,112,932 A | 9/1978 | Chiulli |
| 4,173,350 A | 11/1979 | Sieghartner |
| 4,177,814 A | 12/1979 | Knepshield et al. |
| 4,177,997 A | 12/1979 | Cartwright |
| 4,240,335 A | 12/1980 | Stucka et al. |
| 4,240,411 A | 12/1980 | Hosono |
| 4,311,315 A | 1/1982 | Kronenberg |
| 4,334,688 A | 6/1982 | Spargo et al. |
| 4,338,689 A | 7/1982 | Zieg |
| 4,386,756 A | 6/1983 | Muchow |
| 4,387,879 A | 6/1983 | Tauschinski |
| 4,430,081 A | 2/1984 | Timmermans |
| 4,447,237 A | 5/1984 | Frisch et al. |
| 4,464,178 A | 8/1984 | Dalton |
| 4,492,832 A | 1/1985 | Taylor |
| 4,545,375 A | 10/1985 | Cline |
| 4,553,760 A | 11/1985 | Reed et al. |
| 4,562,838 A | 1/1986 | Walker |
| 4,588,195 A | 5/1986 | Antonini et al. |
| 4,593,691 A | 6/1986 | Lindstrom et al. |
| 4,601,710 A | 7/1986 | Moll |
| 4,626,245 A | 12/1986 | Weinstein |
| 4,641,842 A | 2/1987 | Kataoka |
| 4,654,030 A | 3/1987 | Moll et al. |
| 4,655,752 A | 4/1987 | Honkanen et al. |
| 4,673,393 A | 6/1987 | Suzuki et al. |
| 4,705,511 A | 11/1987 | Kocak |
| 4,715,360 A | 12/1987 | Akui et al. |
| 4,723,550 A | 2/1988 | Bales et al. |
| 4,758,225 A | 7/1988 | Cox et al. |
| 4,827,911 A | 5/1989 | Broadwin et al. |
| 4,827,927 A | 5/1989 | Newton |
| 4,842,591 A | 6/1989 | Luther |
| 4,844,483 A | 7/1989 | Iijima et al. |
| 4,844,484 A | 7/1989 | Antonini et al. |
| 4,857,062 A | 8/1989 | Russell |
| 4,869,717 A | 9/1989 | Adair |
| 4,874,378 A | 10/1989 | Hillstead |
| 4,889,349 A | 12/1989 | Muller |
| 4,909,798 A | 3/1990 | Fleischhacker et al. |
| 4,917,668 A | 4/1990 | Haindl |
| 4,929,235 A | 5/1990 | Merry et al. |
| 4,931,047 A | 6/1990 | Broadwin et al. |
| 4,932,633 A | 6/1990 | Johnson et al. |
| 4,943,280 A | 7/1990 | Lander |
| 4,960,412 A | 10/1990 | Fink |
| 4,966,588 A | 10/1990 | Rayman et al. |
| 4,998,740 A | 3/1991 | Tellier |
| 5,000,745 A | 3/1991 | Guest et al. |
| 5,002,557 A | 3/1991 | Hasson |
| 5,015,000 A | 5/1991 | Perini |
| 5,026,370 A | 6/1991 | Lottick |
| 5,038,756 A | 8/1991 | Kepley |
| 5,041,095 A | 8/1991 | Littrell |
| 5,053,014 A | 10/1991 | Van Heugten |
| 5,053,016 A | 10/1991 | Lander |
| 5,073,169 A | 12/1991 | Raiken |
| 5,085,657 A | 2/1992 | Ben-Simhon |
| 5,088,997 A | 2/1992 | Delahuerga et al. |
| 5,104,383 A | 4/1992 | Shichman |
| 5,127,626 A | 7/1992 | Hilal et al. |
| 5,137,520 A | 8/1992 | Maxson et al. |
| 5,154,709 A | 10/1992 | Johnson |
| 5,167,636 A | 12/1992 | Clement |
| 5,180,373 A | 1/1993 | Green et al. |
| 5,195,959 A | 3/1993 | Smith |
| 5,197,955 A | 3/1993 | Stephens et al. |
| 5,201,714 A | 4/1993 | Gentelia et al. |
| 5,209,736 A | 5/1993 | Stephens et al. |
| 5,209,737 A | 5/1993 | Ritchart et al. |
| 5,217,457 A | 6/1993 | Delahuerga et al. |
| 5,221,264 A | 6/1993 | Wilk et al. |
| 5,226,891 A | 7/1993 | Bushatz et al. |
| 5,234,428 A | 8/1993 | Kaufman |
| 5,242,412 A | 9/1993 | Blake, III |
| 5,244,462 A | 9/1993 | Delahuerga et al. |
| 5,261,918 A | 11/1993 | Phillips et al. |
| 5,290,304 A | 3/1994 | Storace |
| 5,299,813 A | 4/1994 | McKenna |
| 5,300,036 A | 4/1994 | Mueller et al. |
| 5,308,336 A | 5/1994 | Hart et al. |
| 5,313,935 A | 5/1994 | Kortenbach et al. |
| 5,324,270 A | 6/1994 | Kayan et al. |
| 5,342,315 A | 8/1994 | Rowe et al. |
| 5,376,077 A | 12/1994 | Gomringer |
| 5,385,553 A | 1/1995 | Hart et al. |
| 5,395,342 A | 3/1995 | Yoon |
| 5,400,267 A | 3/1995 | Denen et al. |
| 5,407,433 A | 4/1995 | Loomas |
| 5,411,483 A | 5/1995 | Loomas et al. |
| 5,431,650 A | 7/1995 | Cosmescu |
| 5,431,667 A | 7/1995 | Thompson et al. |
| 5,456,284 A | 10/1995 | Ryan et al. |
| 5,496,280 A | 3/1996 | Vandenbroek et al. |
| 5,514,098 A | 5/1996 | Pfoslgraf et al. |
| 5,519,197 A | 5/1996 | Robinson et al. |
| 5,545,142 A | 8/1996 | Stephens et al. |
| 5,634,908 A | 6/1997 | Loomas |
| 5,634,911 A | 6/1997 | Hermann et al. |
| 5,634,937 A | 6/1997 | Mollenauer et al. |
| 5,662,647 A | 9/1997 | Crow et al. |
| 5,667,489 A | 9/1997 | Kraff et al. |
| 5,685,858 A | 11/1997 | Kawand |
| 5,749,871 A | 5/1998 | Hood et al. |
| 5,827,228 A | 10/1998 | Rowe |
| 5,836,944 A | 11/1998 | Cosmescu |
| 6,099,525 A | 8/2000 | Cosmescu |
| 6,402,748 B1 * | 6/2002 | Schoenman et al. ......... 606/45 |

FOREIGN PATENT DOCUMENTS

| | | |
|---|---|---|
| EP | 0051718 | 5/1982 |
| EP | 0113520 | 7/1984 |
| EP | 0312219 | 4/1989 |
| GB | 1482857 | 8/1977 |
| WO | WO9304717 | 3/1993 |
| WO | WO9513023 | 5/1995 |
| WO | WO9604936 | 2/1996 |
| WO | WO9740761 | 11/1997 |
| WO | WO9853865 | 12/1998 |

* cited by examiner

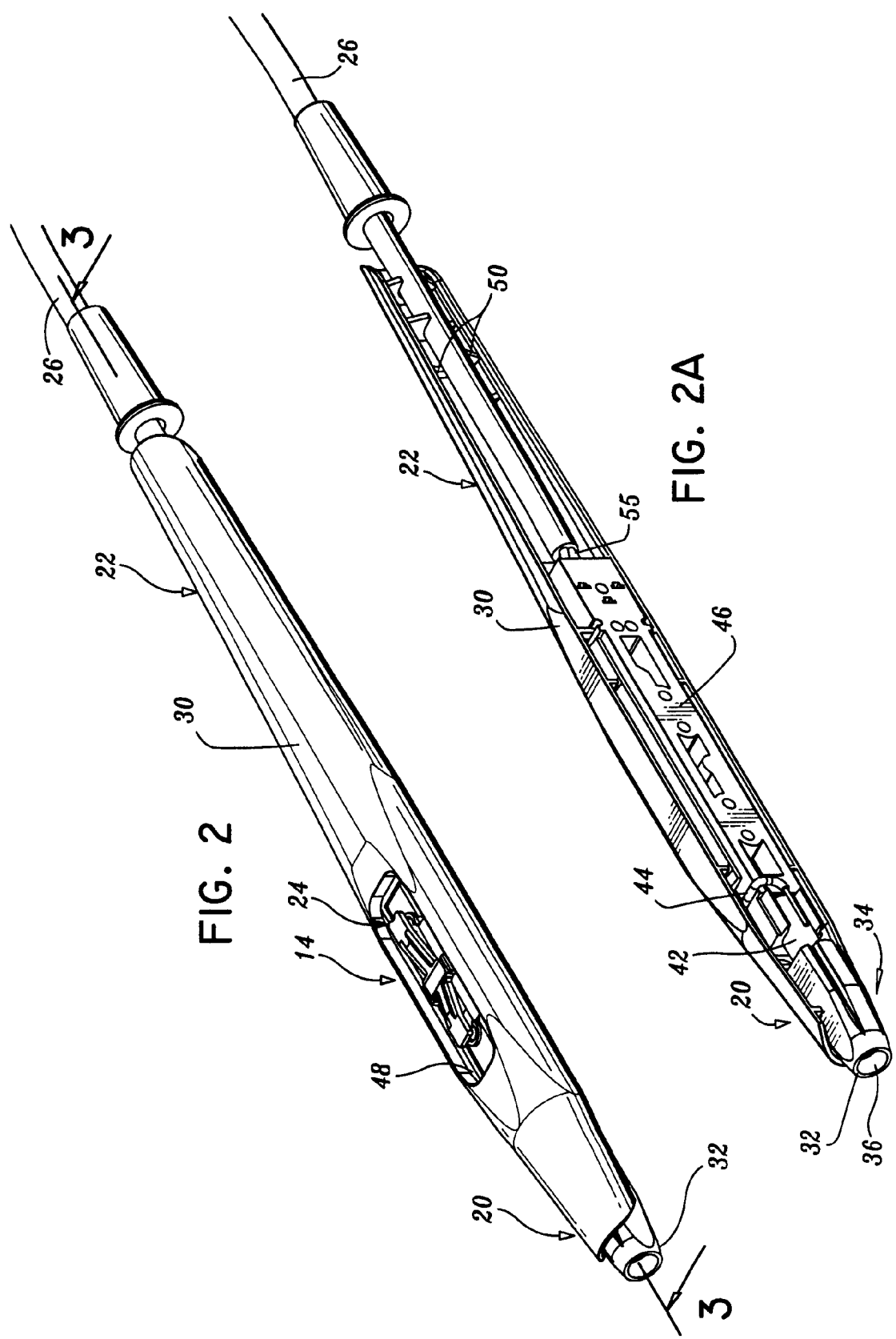

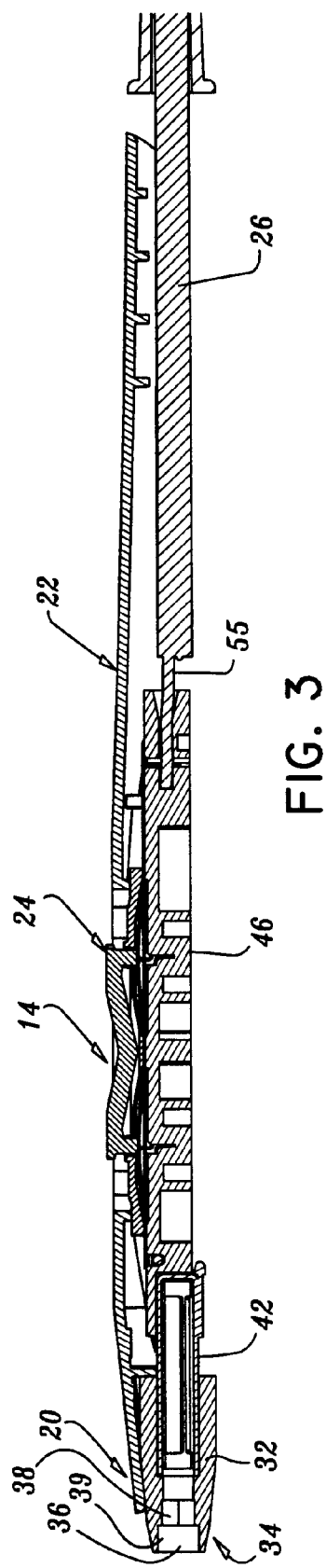
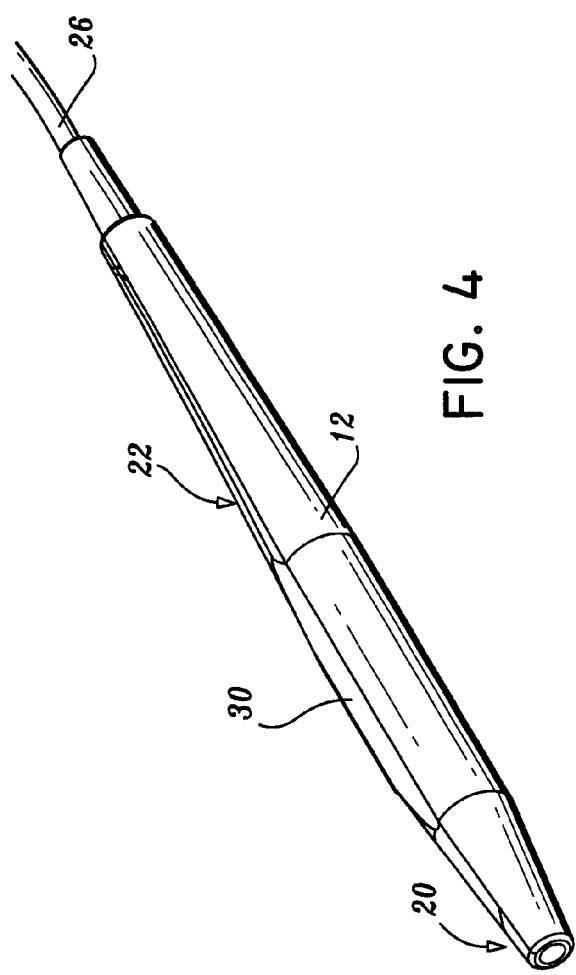

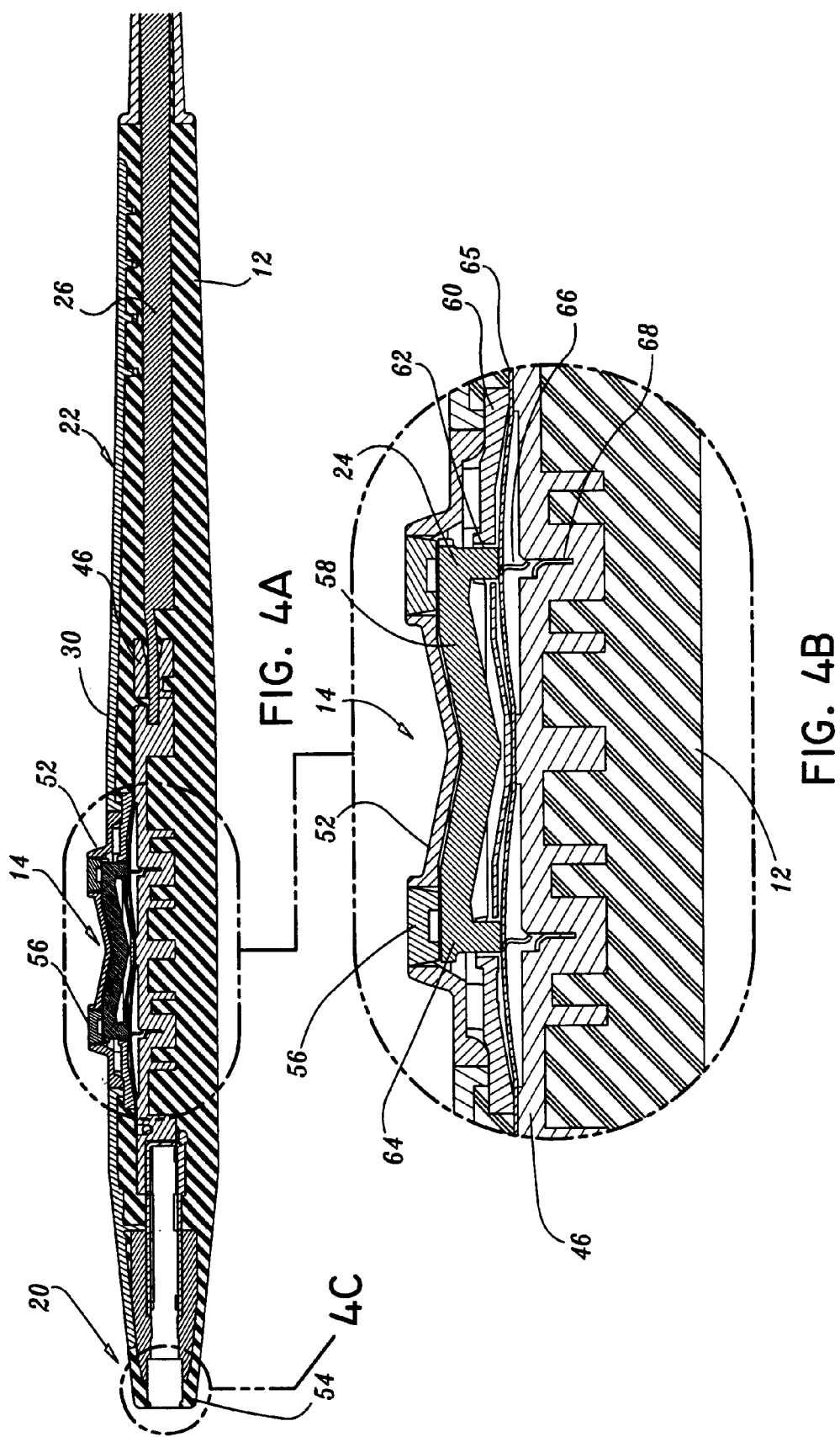

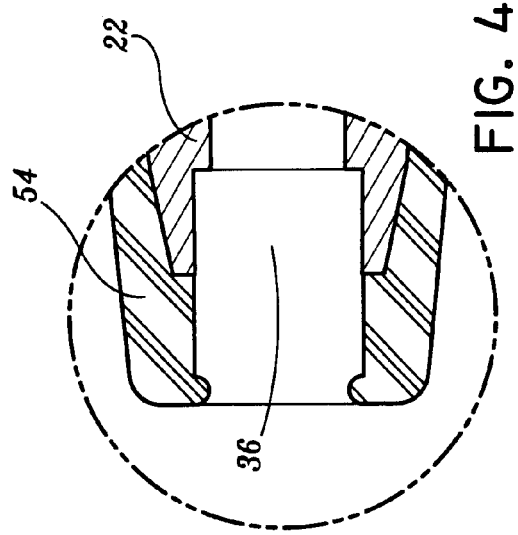
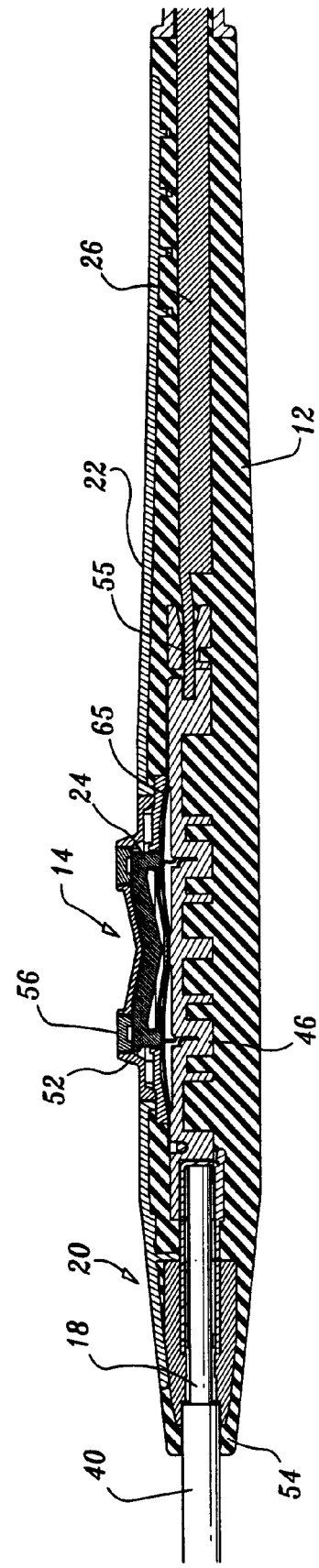
FIG. 4C
FIG. 4D

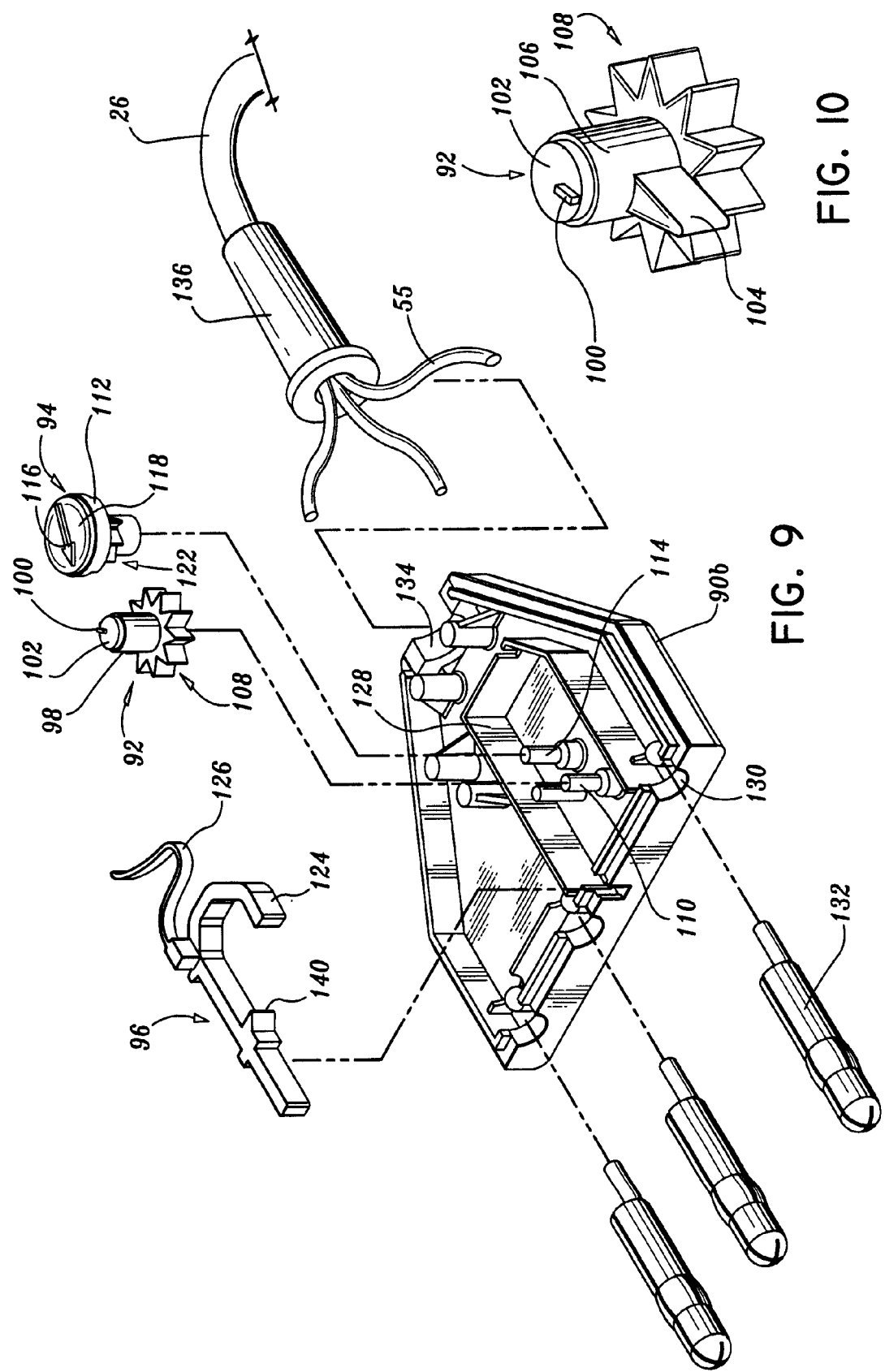

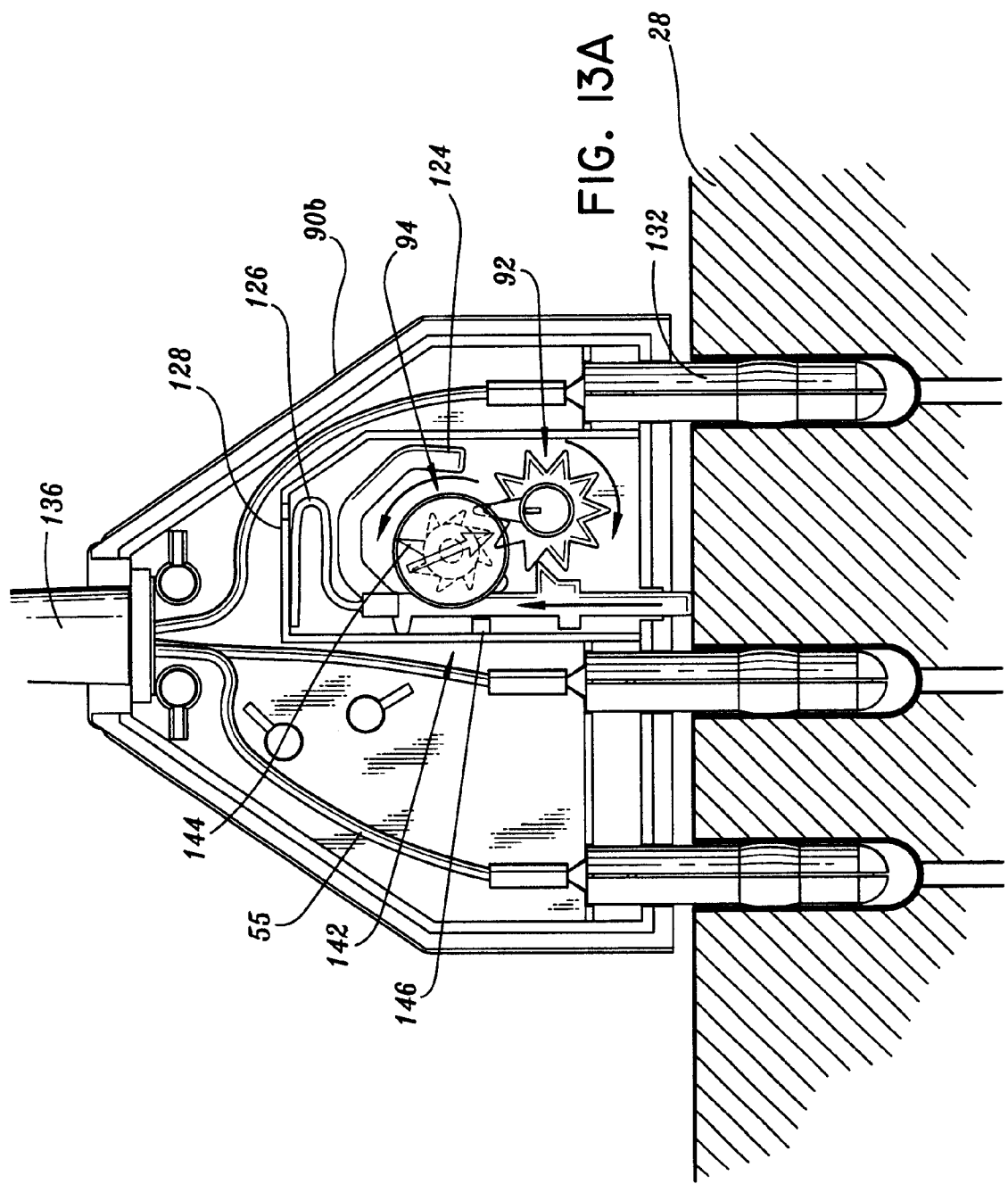

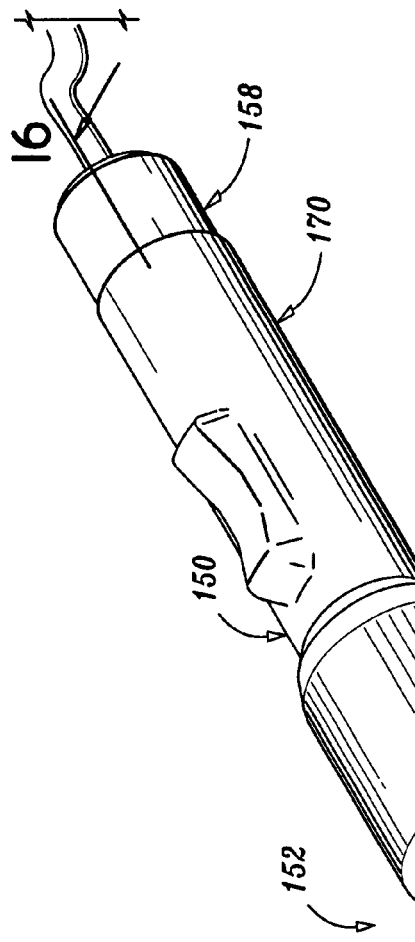
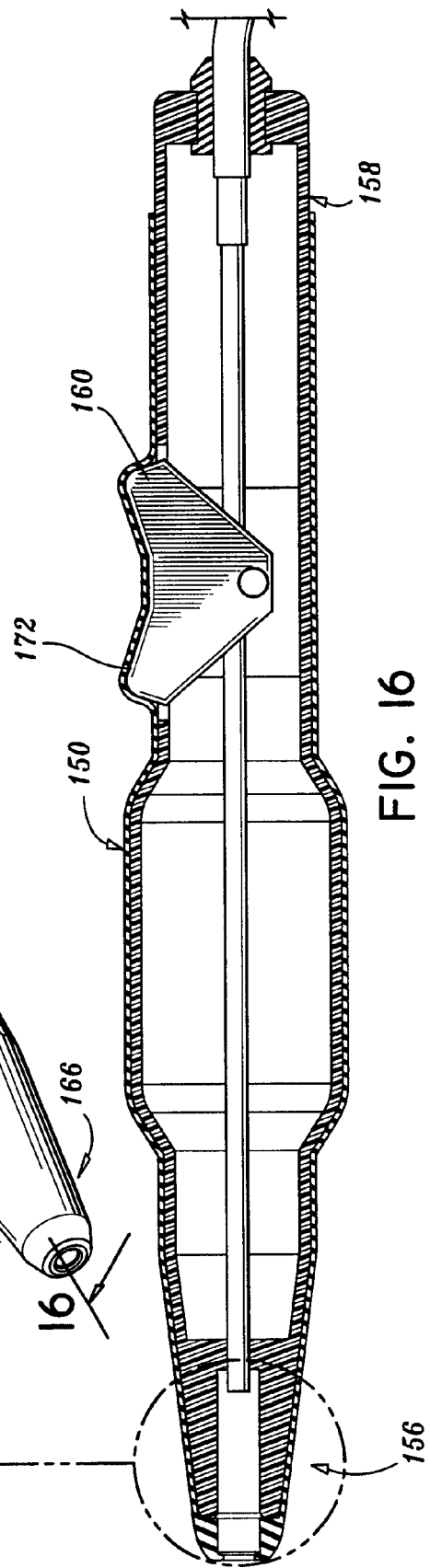
FIG. 15
FIG. 16

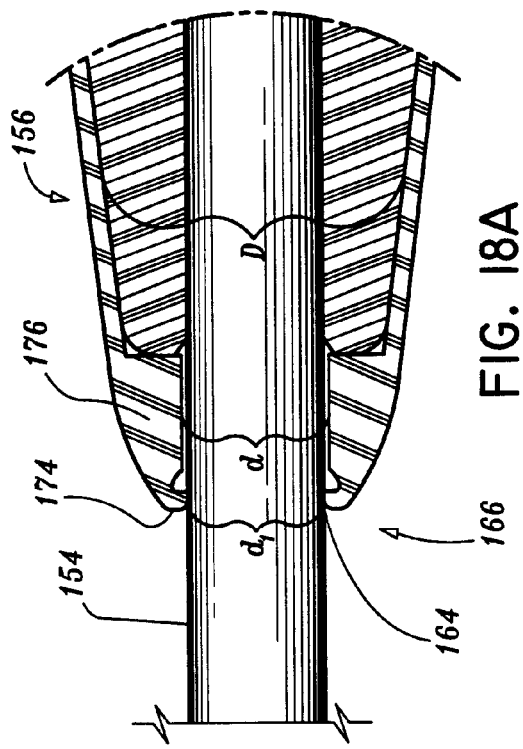
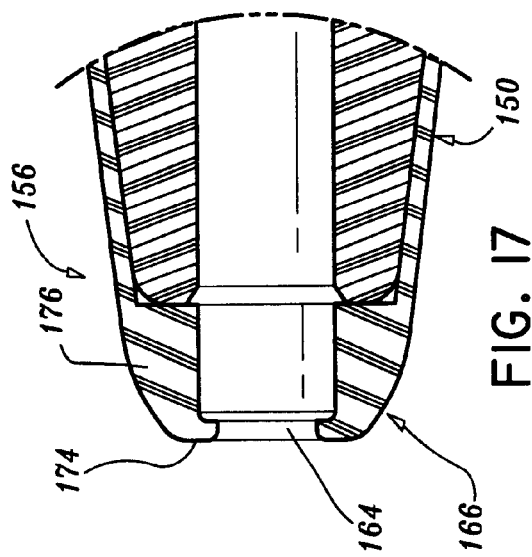
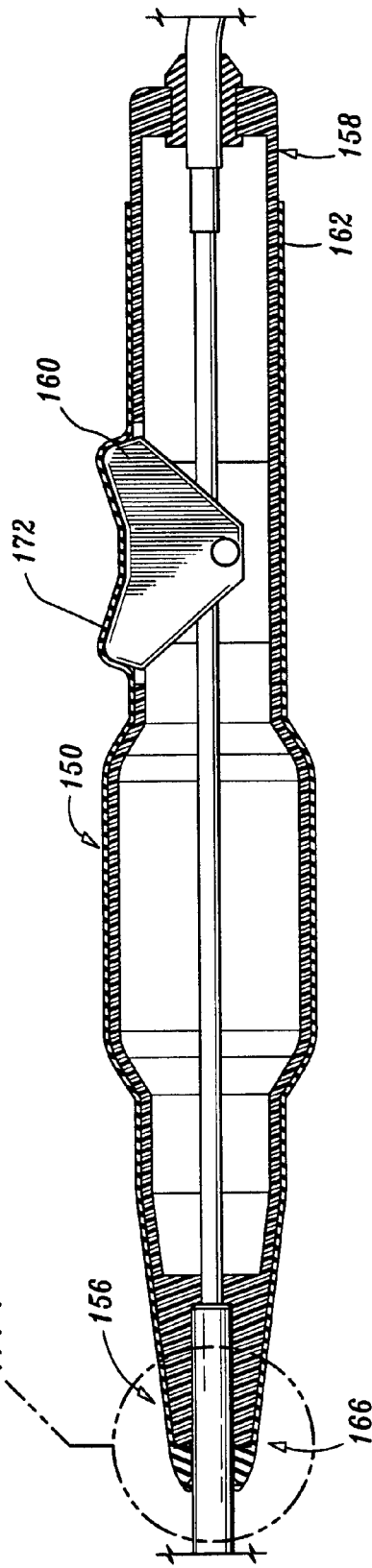

US 6,755,825 B2

ELECTROSURGICAL DEVICE HAVING A DIELECTRIC SEAL

This application is a division of Ser. No. 09/396,897 filed Sep. 15, 1999, and claims benefit of 60/105,367 Oct. 23, 1998.

BACKGROUND

1. Technical Field

This disclosure relates generally to an electrosurgical device of the type having an actuator for alternating between a cauterizing and a cutting mode. More particularly, the present disclosure relates to an electrosurgical device having an elastomeric seal for providing bio-contamination and dielectric protection by preventing fluids from entering the nose and actuator areas of the electrosurgical device.

2. Background of the Related Art

Electrosurgical devices suitable for use in surgical procedures such as cauterizing, cutting and similar procedures are well known. For example, U.S. Pat. Nos. 3,648,001; 3,801,766; 4,827,911; 4,827,927; 5,088,997; 5,217,457; and 5,244,462, the contents of which are incorporated herein by reference, disclose such electrosurgical devices. Typically, these electrosurgical devices introduce RF cauterizing current, cutting current, or a blend thereof to a conductive blade inserted within a nose area of a longitudinal housing by means of a finger-operated switch actuating member disposed on the housing and electrically coupled to the electrode and a generator. Optionally, such devices include suction and irrigation capabilities. These features are typically controlled through control mechanisms contained within the electrosurgical device and are actuated with the actuating member or some other actuator disposed on the housing or on the generator.

In some procedures, the advancement of the blade into body tissue to perform a surgical procedure causes fluids and bio-materials to collect near the device adjacent the nose or actuator areas. These fluids and bio-materials may deposit on the control mechanisms and wires within the housing thereby making it difficult to sterilize and reuse the device. Additionally, conductive fluids can provide an undesirable conductive path from the electrode to the surgeon and other objects in the surgical site, if fluid enters the nose or actuator areas.

Accordingly, a need exists for an electrosurgical device where the main operating components and mechanisms are provided within a sealed environment to provide bio-contamination and dielectric protection. A need further exists for a method of manufacturing an electrosurgical device where the method provides at least one seal for the electrosurgical device. Another need which exists is for an electrosurgical device having a counting mechanism for indicating to an operator the number of times the device has been plugged into an electric generator. Still, a need exists for the counting mechanism to have a disable mechanism for preventing the electrosurgical device from being plugged into the electric generator after a predetermined amount of insertion and removal operations. A need also exists for a seal that can be easily applied to an electrosurgical device, is inexpensive, simple and reliable and which provides bio-contamination and dielectric protection by inhibiting the ingress of fluids and contaminants through the nose and actuator areas. A need further exists for a seal that provides bio-contamination and dielectric protection by inhibiting the ingress of fluids and contaminants through the nose and actuator areas.

SUMMARY

In accordance with the present disclosure, an electrosurgical device is provided having at least one elastomeric seal capable of providing bio-contamination and dielectric protection by inhibiting the ingress of fluids and contaminants through the nose and actuator areas. The electrosurgical device is of the type used to perform cauterizing and cutting of body tissue by means of a finger-actuated switch actuating means. The elastomeric seal is manufactured from a thermoplastic elastomer or resin which is placed in liquid form within a mold. A housing partial-section having the main circuit components and mechanisms of the electrosurgical device is then placed within the mold. Once the elastomer cures, the elastomeric seal seals the components and mechanisms within the housing partial-section. The elastomeric seal defines a flexible first opening at a distal end of the electrosurgical device to accommodate varying diameters of electrodes or blades connected to the nose area of the electrosurgical device.

An actuator seal is also provided on the actuator area of the electrosurgical device to prevent fluids and contaminants from entering the electrosurgical device through the actuator area. Two buttons are insert molded within the actuator seal and are operatively associated with a self-cleaning switching mechanism within the housing partial-section to operate the electrosurgical device between a cutting and coagulating mode. The actuator seal is also manufactured from a thermoplastic elastomer or resin.

The preferred self-cleaning switching mechanism includes a switch contact plate having pair of movable contacts with contact faces. Each movable contact corresponds to a stationary contact positioned within a circuit mold. Each stationary contact has a contact face aligned with a respective contact face of the corresponding movable contact. As the actuator seal is depressed, contact faces of the movable and stationary contacts slide along each other to clean the contacts of, e.g., non-conductive corrosion and contaminants.

The electrosurgical device is further provided with a counting mechanism for counting the number of times the device is plugged into an electric generator. The counting mechanism is included at the proximal end of an electrical cord electrically connecting circuitry within the electrosurgical device and the electric generator.

Further, in accordance with the present disclosure, an elastomeric seal is disclosed which is manufactured separately from an electrosurgical device it is intended to seal. The seal defines a first opening at a distal end and a second opening at a proximal end for fitting the elastomeric seal over the electrosurgical device. An actuating member pocket is defined in proximity to the second opening for fitting the actuating member therein. The seal further includes a lip portion having an elastic wall circumferentially surrounding the first opening to accommodate varying diameters of electrodes.

In an alternate embodiment, an elastomeric seal is chemically adhered, if the seal is desired to be reusable, or mechanically attached, if the seal is desired to be disposable, to the nose area of an electrosurgical device to prevent fluids and bio-materials from entering the nose area and preventing establishment of a conductive path. It is contemplated that the seal can be friction fit to the nose area of the electrosurgical device as well. Preferably, the elastomeric seal includes a soft lip to permit electrodes and blades of varying diameters to be inserted and sealed.

BRIEF DESCRIPTION OF THE DRAWINGS

A preferred embodiment is described herein with reference to the drawings, wherein:

FIGS. 2 and 2A are perspective views of the electrosurgical device of FIG. 1 without the elastomeric seal;

FIG. 3 is a cross-sectional view taken along line 3—3 of FIG. 2;

FIG. 4 is a perspective view showing the bottom of the electrosurgical device of FIG. 1;

FIG. 4A is a cross-sectional view of the electrosurgical device of FIG. 1;

FIG. 4B is an enlarged view of the switch area shown in FIG. 4A;

FIG. 4C is an enlarged view of the tip area shown in FIG. 4A;

FIG. 4D is a cross-sectional view of the electrosurgical device of FIG. 1 having an electrode attached thereto;

FIG. 9 is an exploded, assembly view of the plug connector detailing the counting mechanism;

FIG. 10 is an enlarged, perspective view of the rotary gear of the counting mechanism;

FIG. 13A is an alternative embodiment of the counting mechanism;

FIG. 15 is a perspective view of the elastomeric seal of FIG. 14 in place over an electrosurgical device;

FIG. 16 is a cross-sectional view taken along line 16—16 in FIG. 15;

FIG. 17 is an enlarged view of the tip area of the electrosurgical device shown in FIG. 16;

FIG. 18 is a cross-sectional view of the electrosurgical device of FIG. 15 having an electrode attached thereto;

FIG. 18A is an enlarged view of the electrode interface area of the electrosurgical device shown in FIG. 18;

DETAILED DESCRIPTION OF PREFERRED EMBODIMENTS

Figure 1:
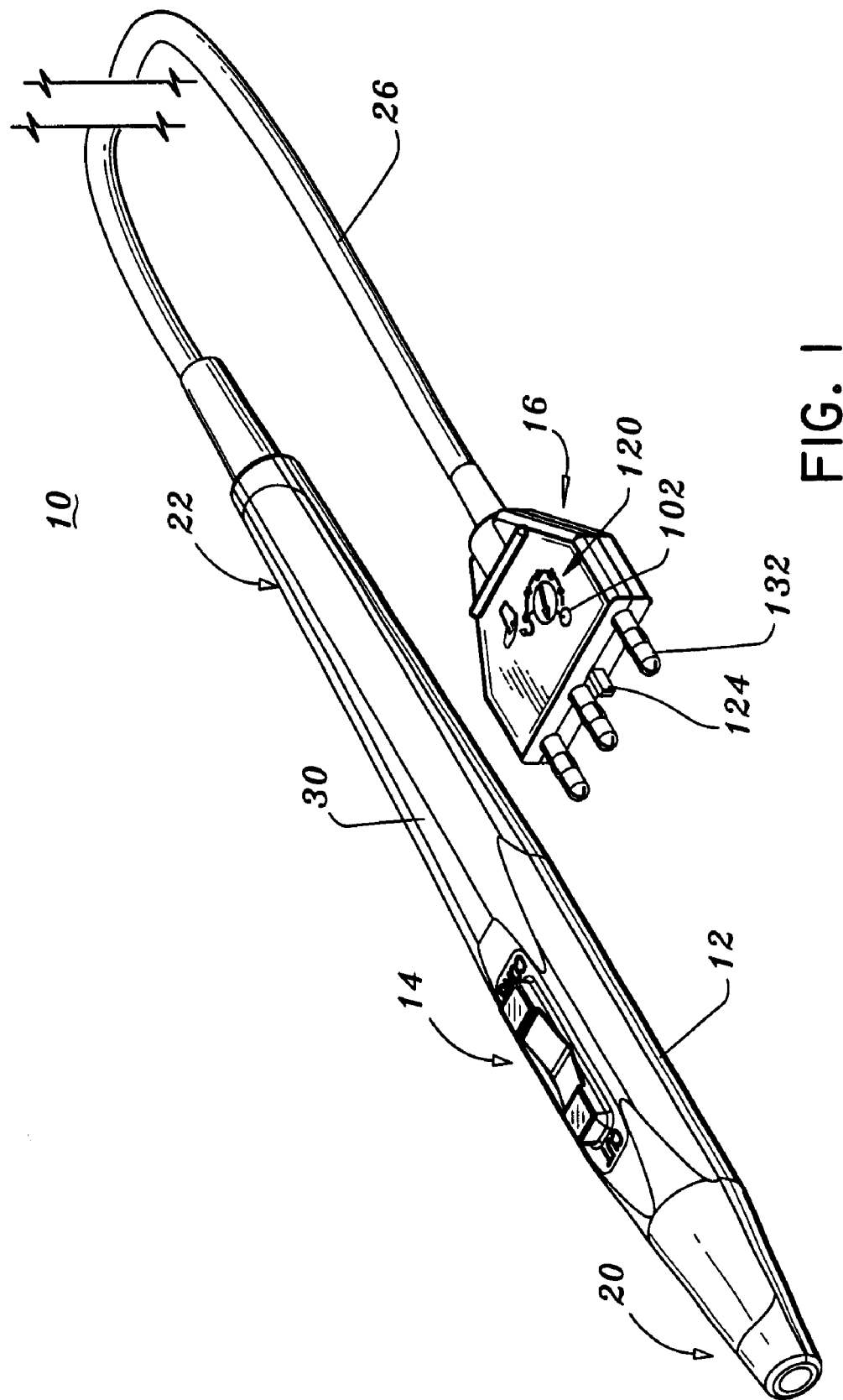
FIG. 1 is a perspective view of an electrosurgical device having an elastomeric seal and a counting mechanism according to the present disclosure.

An electrosurgical device having a seal formed integrally with the electrosurgical device and two embodiments of an elastomeric seal for a standard electrosurgical device will now be described in detail with reference to the drawings, in which like reference numerals designate identical or corresponding elements in each of the several views. A self-cleaning switching mechanism and a counting mechanism for the electrosurgical device having the seal formed integrally therewith are also described.

While the electrosurgical device having a seal formed integrally therewith and the two embodiments of the elastomeric seal of this disclosure are useful to provide biocontamination and dielectric protection, particularly in arthroscopic procedures where there are large amounts of fluid at the surgical site, by preventing fluid from entering the nose and actuator areas of the electrosurgical device disclosed herein or other standard electrosurgical devices, other functions such as inhibiting contamination of the device or the devices the seals are fitted onto are also contemplated.

With reference to FIGS. 1–13, a preferred embodiment of an electrosurgical device having an integrally formed seal, a self-cleaning switching mechanism and a counting mechanism which counts the number of times the device is plugged into an electric generator will now be described. FIG. 1 illustrates the electrosurgical device designated generally by reference numeral 10 having an elastomeric seal 12, a self-cleaning switching mechanism 14 and a counting mechanism 16. Electrosurgical device 10 is suitable for use in surgical procedures such as cauterizing, cutting and similar procedures. Electrosurgical device 10 introduces RF cauterizing current, cutting current, or a blend thereof to an electrode 18 (FIG. 4D) protruding from a nose area 20 by means of self-cleaning switching mechanism 14 disposed within housing partial-section 22. Device 10 can be sterilized by accepted sterilization techniques such as, for example, autoclaving or EtO.

Self-cleaning switching mechanism 14 includes a rocker switch 24 capable of operating device 10 between a cutting mode and a coagulating mode. Counting mechanism 16 is included at a proximal end of electrical cord 26 for counting the number of times device 10 is plugged into an electrical generator 28. Electrical cord 26 preferably includes a silicone extruded jacket having three polytetrafluoroethylene insulated conductors therein and is approximately 4.5 meters in length. Switching mechanism 14 is further described below with reference to FIGS. 4A and 4B and counting mechanism 16 is further described below with reference to FIGS. 7–13.

With reference to FIGS. 2–3, housing partial-section 22 includes an elongated body portion 30 supporting a tubular member 32 at a distal end 34. Although shown as a housing half-section, other configurations of the housing are also contemplated such as third sections, quarter sections, full sections, etc. Tubular member 32 includes a bore 36 therethrough having a female hex 38 in proximity to a female electrode receptacle 39 which receives electrode sleeve 40 (FIG. 4D). It is contemplated that receptacle 39 can effectively retain a 3/32 inch diameter shank electrode from 0.6 to 0.9 inches in exposed length. An electrode's molded hex feature is inserted into receptacle 39 to prevent electrode 18 from rotating.

A metallic tube member 42 matingly engages one end of tubular member 32. A distal portion of electrode 18 matingly engages metallic tube member 42 when electrode 18 is inserted within tubular member 32. Metallic tube member 42 also makes contact with a wire 44 embedded within molding 46 to energize metallic tube member 42 and in turn energize electrode 18 upon depression of rocker switch 24 as further described below.

Body portion 30 includes an actuating member pocket 48 for exposing rocker switch 24 as shown by FIG. 2. Body portion 30 further includes several protrusions 50 at a proximal end for supporting electric cord 26 as shown by FIG. 2A.

Elastomeric seal 12 is formed in and around housing partial-section 22 to seal the various components and the self-cleaning switching mechanism 14 within housing partial-section 22 and form device 10 as shown by FIGS. 1 and 4. An elastomeric actuator switch seal 52 is also formed in and around rocker switch 24. It is contemplated that actuator switch seal 52 provides a tactile response to the operator upon contact closure in either of the two positions: CUT or COAG (FIG. 1).

The formation of seal 12 entails introducing polypropylene within the bottom of body portion 30 of housing partial-section 22 to fill body portion 30 and add stiffness to electrosurgical device 10. Second, the polypropylene filled housing partial-section 22 is overmolded with a polypropylene-based thermoplastic elastomer to form the final outer shape of device 10 including a soft lip 54 (FIG. 4C) around nose area 20 to maintain electrode sleeve 40 in place while preventing fluids from entering nose area 20.

In forming actuator seal 52, a pair of contact inserts 56 are positioned such that a contact insert 56 coincides with each end of actuating member pocket 48. Polypropylene is then added to form actuator seal 52 and to also insert mold inserts 56 within seal 52. One insert is colored yellow to designate the cutting mode and the other insert is colored blue to designate the coagulating mode. Preferably, the color yellow is used to identify the cutting insert and the color blue is used to identify the coagulating insert.

With reference to FIGS. 4A and 4B, self-cleaning switching mechanism 14 will now be described in greater detail. Each insert 56 which is insert molded within actuator seal 52 corresponds to a respective rocker arm 58 of rocker switch 24. Rocker switch 24 is held in place by a support plate 60 which is press-fitted within housing partial-section 22. Support place 60 includes two openings 62 in alignment with a respective protrusion 64 from rocker switch 24. Each protrusion 64 is capable of contacting a switch contact plate 65 (see FIGS. 6A and 6B) which includes a pair of moving contacts 66 which engage a corresponding stationary contact 68 when rocker switch 24 is depressed for facilitating cutting or coagulating. Cutting is facilitated if the yellow insert is depressed and coagulating is facilitated if the blue insert is depressed.

Figure 5:
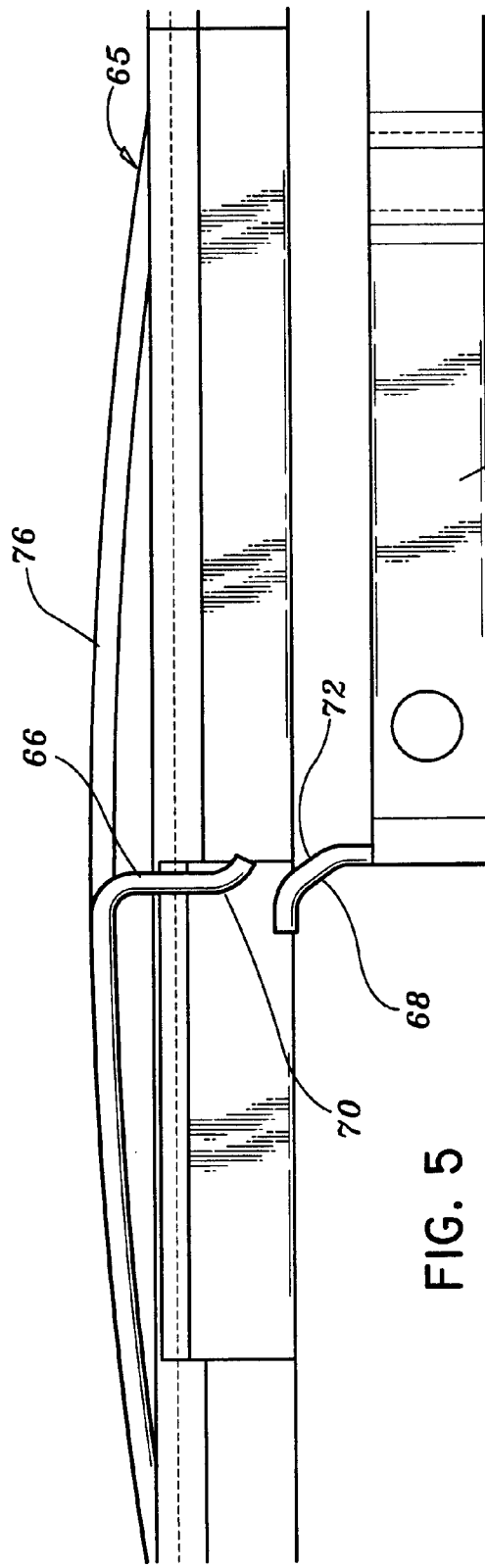
FIG. 5 is an enlarged, side view of the self-cleaning switching mechanism of the electrosurgical device shown in FIG. 1.
Figure 6:
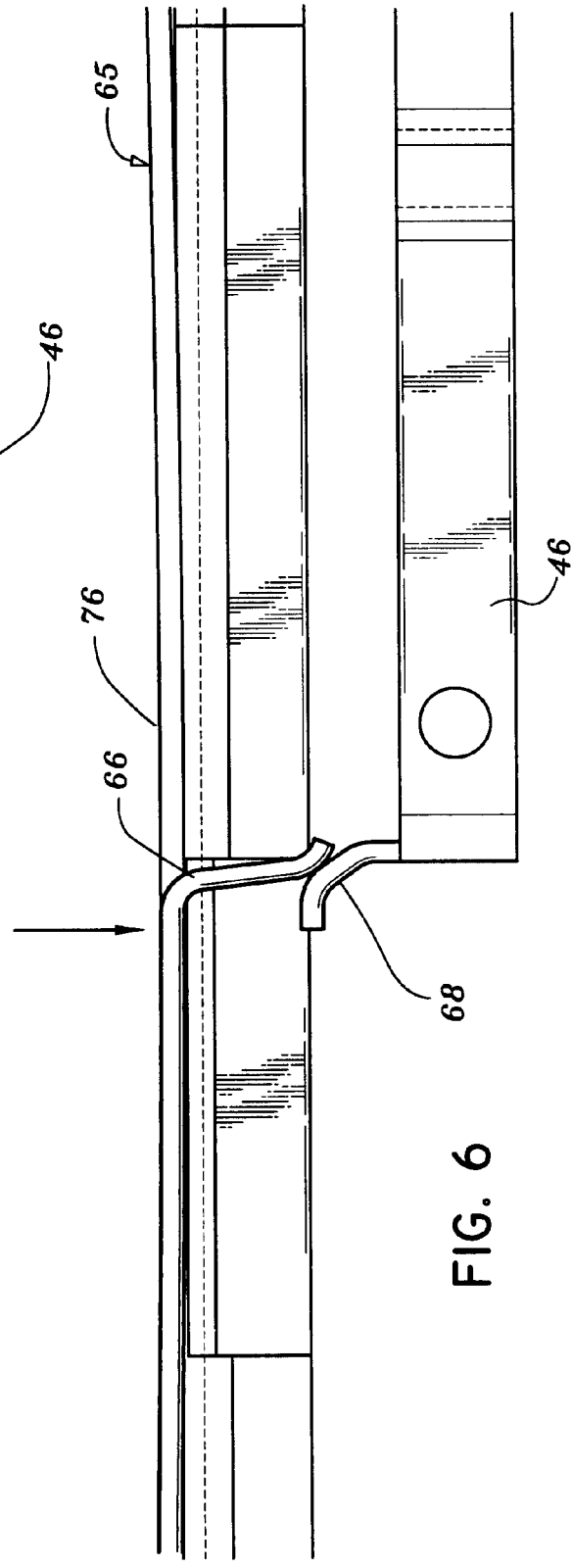
FIG. 6 is an enlarged, side view of the self-cleaning switching mechanism being depressed to actuate the electrosurgical device shown in FIG. 1.

As seen in FIGS. 5 and 6, to facilitate self-cleaning of contact faces 70 of moving contacts 66 and of contact faces 72 of stationary contacts 68, stationary contacts 68 are angled with respect to moving contacts 66 and moving contacts 66 are slightly flexible so that contact faces 70 slide across contact faces 72 during operation of switching mechanism 14. This eliminates buildup of non-conductive corrosion and contaminants on contact faces 50 and 52 during operation of electrosurgical device 10.

Figure 6A:
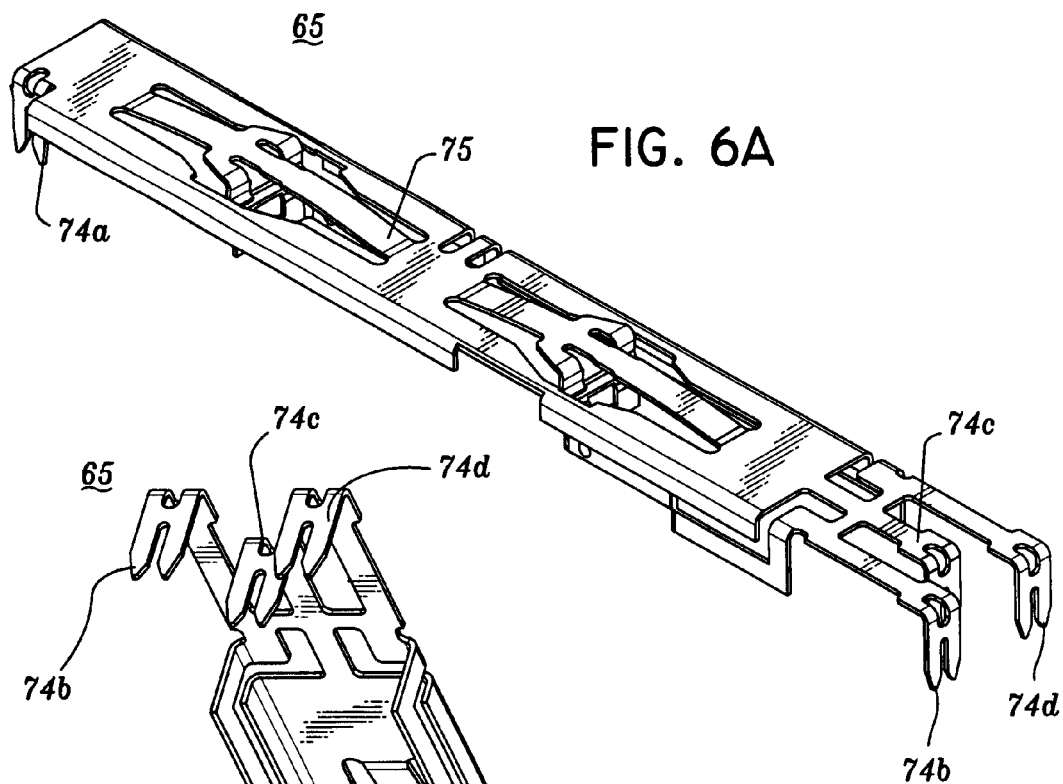
FIGS. 6A and 6B are enlarged, perspective views of a switch contact plate having a pair of moving contacts.
Figure 6B:
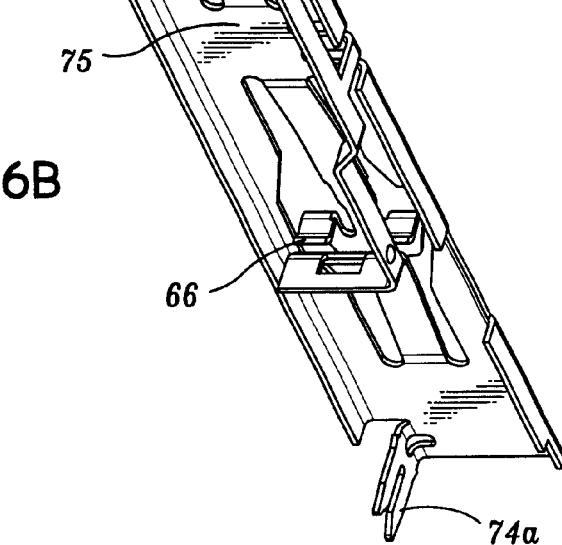
Figure 8:
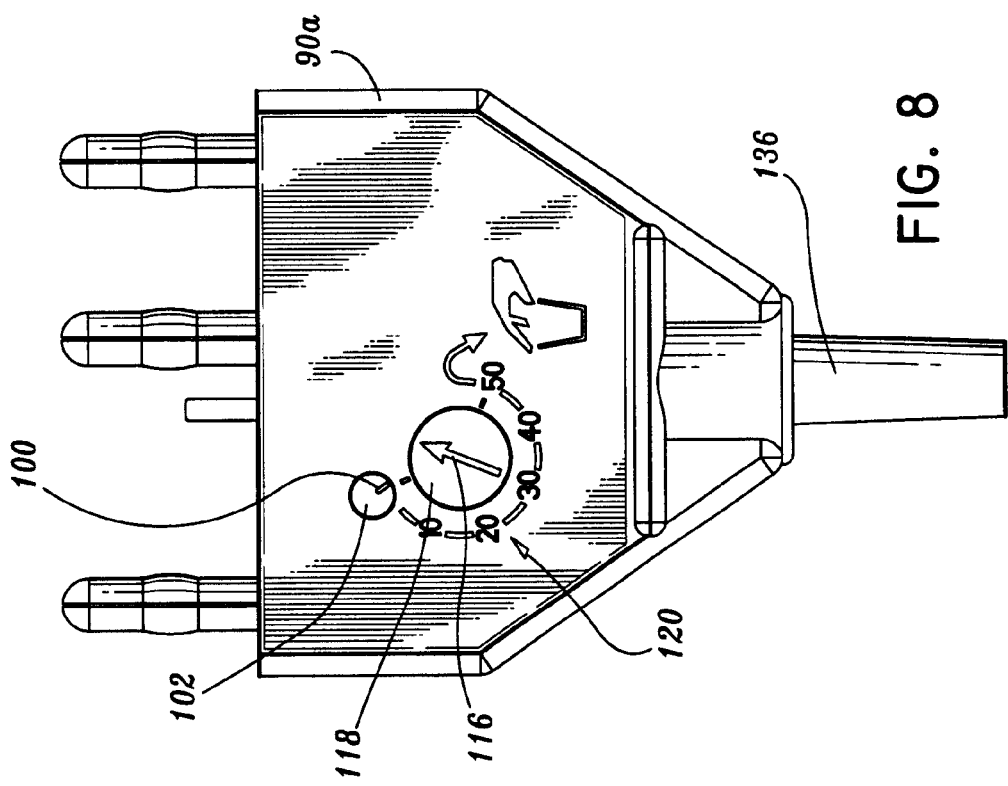
FIG. 8 is an enlarged, top view of the plug connector of FIG. 7.
Figure 7:
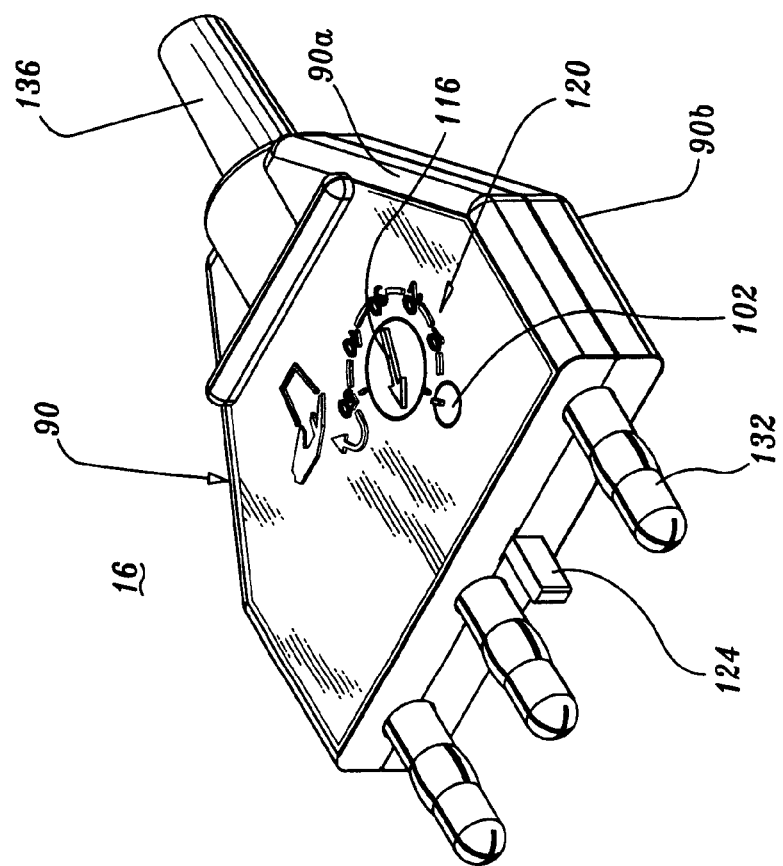
FIG. 7 is an enlarged, perspective view of the plug connector with an integral counting mechanism shown in FIG. 1.

With reference to FIGS. 6A and 6B, switch contact plate 65 includes prongs 74 on both ends for embedding plate 65 within molding 46 (FIGS. 4A and 4D). One prong 74A makes contact with wire 44 and other prongs 74B, 74C and 74D make contact with wires 55 to provide cutting and coagulating electrical connections between wires 55 and electric generator 28. It is noted that prong 74C is connected to wire 44 via central connection or power bus 75 to provide grounding for both the cutting and coagulating electric circuits.

Switch contact plate 65 further includes two rounded portions 76 capable of making contact with protrusions 64 of rocker arms 58. Rounded portions 76 flex downwards when rocker switch 24 is depressed to cause one of the two moving contacts 66 to contact its corresponding stationary contact 68 and create an electrical connection between wires 55, power bus 75, wire 44 and electric generator 28.

Counting mechanism 16 will now be described with reference to FIGS. 7–13. Counting mechanism 16 is provided within a plug connector 88. Plug connector 88 includes a housing 90 having housing half-sections 90a and 90b for housing various components of counting mechanism 16 therein. Counting mechanism 16 includes a rotary gear 92, a counting gear 94, and a spring-biased member 96. Rotary gear 92 (FIG. 10) includes a cylindrical head 98 having a marker 100 on a top surface 102 and a contact member 104 protruding from a lateral surface 106. A gear wheel 108 is connected to one end of rotary gear 92. Rotary gear 92 is designed to matingly engage a first cylindrical member 110 on housing half-section 90b.

Counting gear 94 includes a circular head 112 designed to matingly engage a second cylindrical member 114 on housing half-section 90b. Circular head 112 includes an arrow 116 on a top surface 118 for pointing to a counting sequence 120 on housing half-section 90a as counting gear 94 is rotated as further described below. Counting gear 94 also includes a gear wheel 122 underneath circular head 112. Spring-biased member 96 includes a cane-shaped member 124 and a spring 126. Spring 126 is designed to rest upon a section of bar member 128 when counting mechanism 16 is not plugged within electric generator 28.

Figure 12:
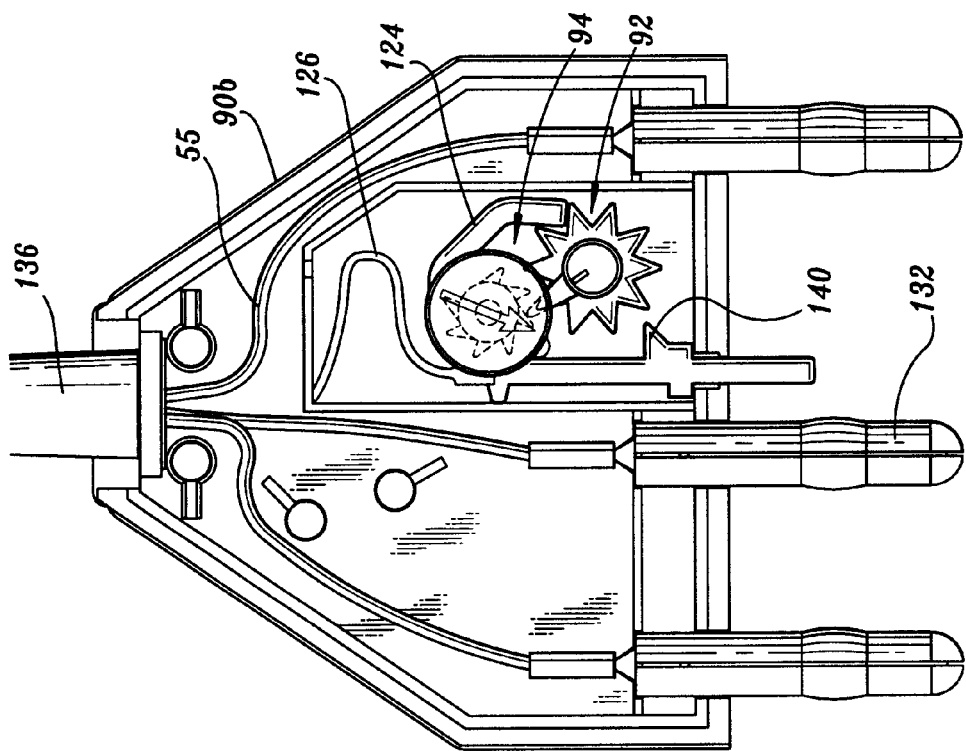
FIG. 12 is a top view of the inner components of the plug connector showing the counting mechanism.
Figure 11:
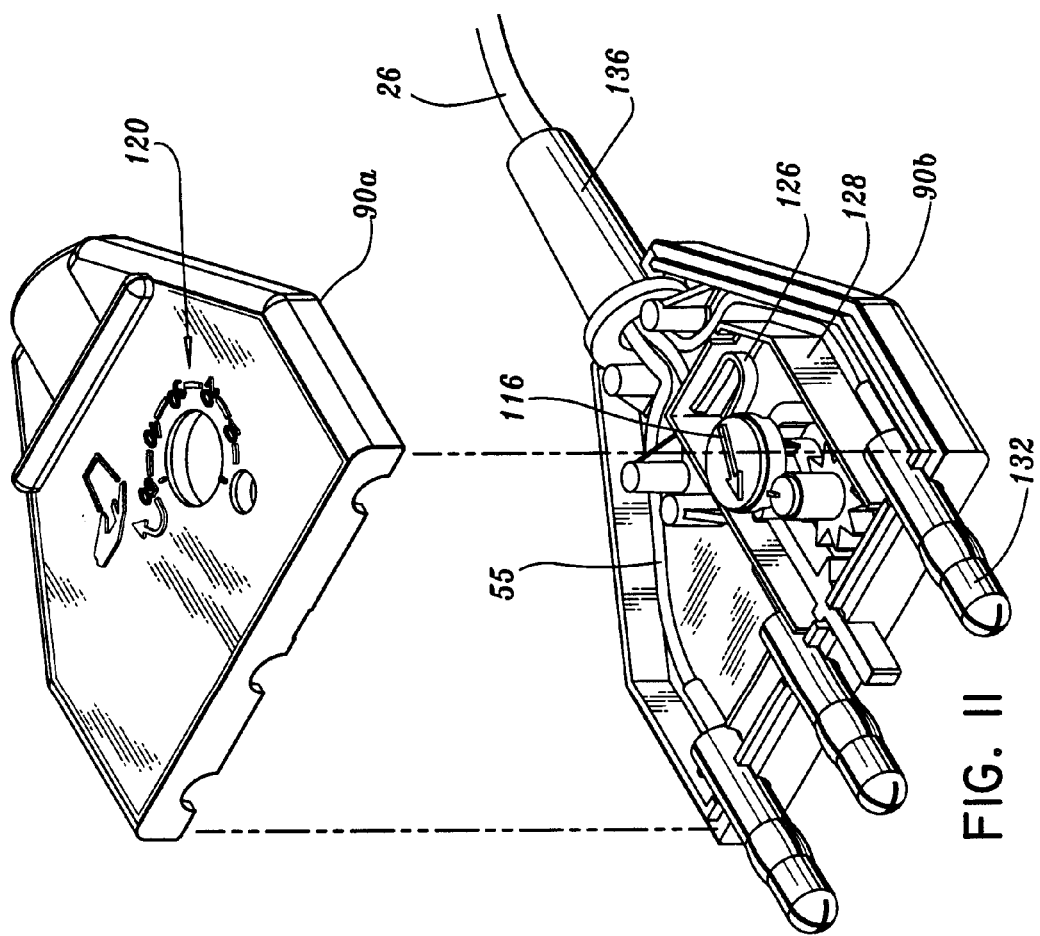
FIG. 11 is an enlarged, assembly view of the plug connector with the top half-section of the housing removed.

Housing 90 further includes three openings 130 for placement of prongs 132 therein for creating an electrical connection between electric generator 28 and electrosurgical device 10. Another opening 134 is also included for placement of a tubular cord housing 136 housing a proximal end of electrical cord 26. Wires 55 extend from the proximal end of electrical cord 26 and are each electrically coupled to a corresponding prong 132 as shown by FIG. 12.

Figure 13:
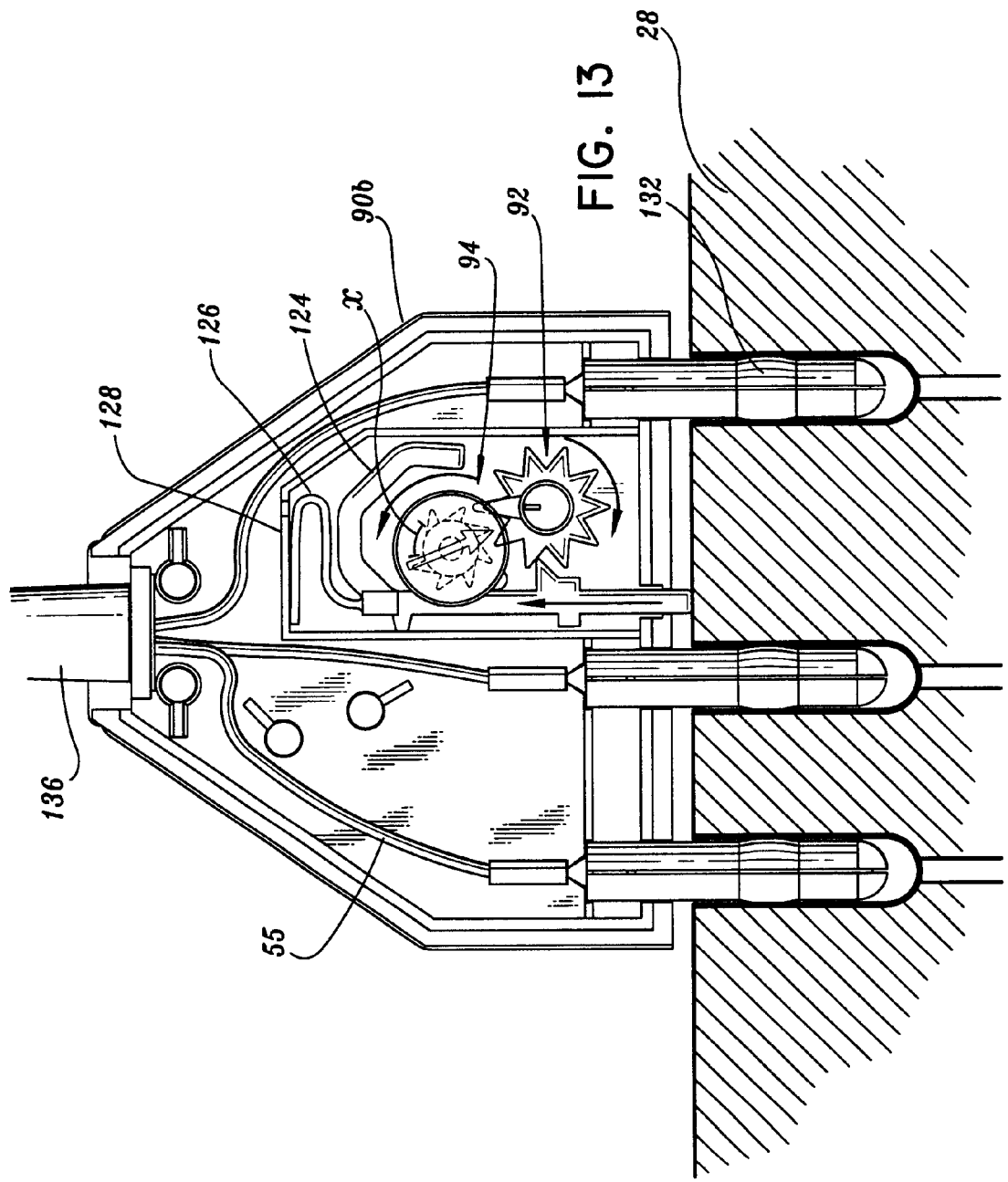
FIG. 13 is a top view of the inner components of the plug connector and counting mechanism when the plug connector is inserted within the electric generator.

When prongs 132 are plugged into electric generator 28, the distal end of cane-shaped member 124 contacts electric generator 28 and is forced proximally to push spring 126 against bar member 128 (FIG. 13). As cane-shaped member 124 moves proximally, a protrusion 140 makes contact with gear wheel 108 to turn rotary gear 92 clockwise. Consequently, as rotary gear 92 turns clockwise, contact member 104 makes contact with gear wheel 122 to cause counting gear 94 to turn counter-clockwise. This causes arrow 116 to point to a different position on counting sequence 120. When counting mechanism 16 is removed from the electric generator 28, spring 126 springs back to move cane-shaped member 124 distally.

After a predetermined amount of insertion and removal operations of counting mechanism 16, a point identified as "X" on gear wheel 122 (FIG. 13) comes in proximity to rotary gear 92. Point "X" does not include a gear for contact member 104 to contact and cause the rotation of counting gear 96. Consequently, counting gear 96 remains stationary with arrow 116 pointing to the end of counting sequence 120, thereby notifying the operator to dispose electrosurgical device 10 as indicated by the icon (hand and trash bin) on housing half-section 90a. It is contemplated that rotary gear 92 and counting gear 94 may be positioned during manufacturing such that point "X" comes in proximity to contact member 104 after a predetermined amount of insertion and removal operations, and not necessarily when arrow 116 points to the end of counting sequence 120. Although shown herein as a mechanical or analog mechanism, it is also contemplated that the counter/disable mechanism can be electrical, magnetic, etc.

FIG. 13A depicts an alternative plug connector having a disable mechanism 142 for preventing the plug connector from being plugged into the electric generator after a pre-determined amount of insertion and removal operations. Disable mechanism 142 includes a sprocket 144 on gear wheel 122 which engages protrusion 146 on bar member 128 to prevent gear wheel 122 from turning counter-clockwise after gear wheel 122 has moved a pre-determined number of times. When sprocket 144 engages protrusion 146, cane-shaped member 124 does not move proximally upon insertion into electric generator 28, since gear wheel 108 is prevented from turning upon contact with protrusion 140.

Figure 14:
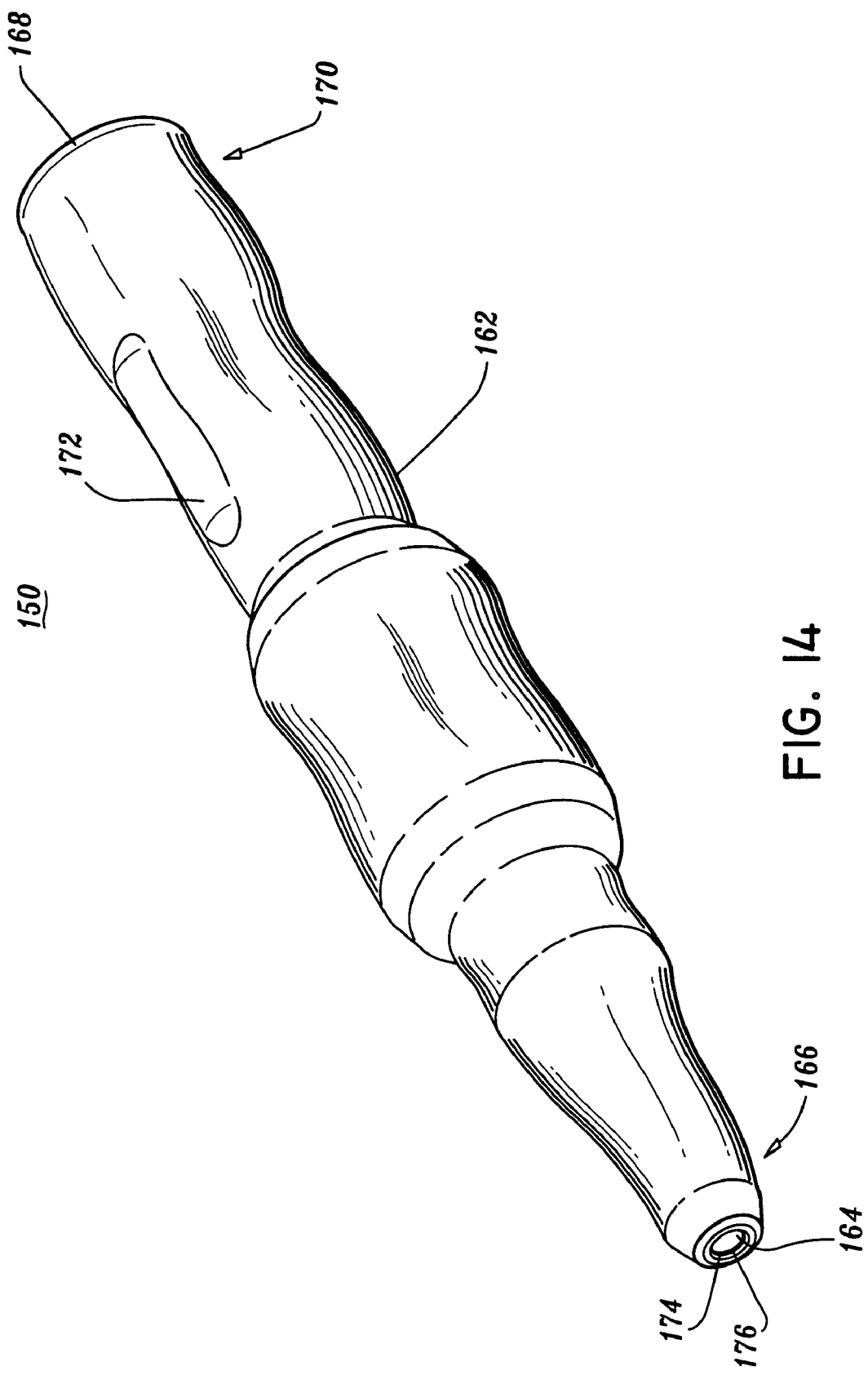
FIG. 14 is a perspective view of an elastomeric seal configured to fit over an electrosurgical device.

With reference now to FIGS. 14–18, an elastomeric seal of a first embodiment will be described which is designated generally by reference numeral 150. Seal 150 of FIG. 14 is designed to fit upon a standard electrosurgical device of the type shown by FIG. 15 and designated generally by reference numeral 152. Similarly to electrosurgical device 10, electrosurgical device 152 is suitable for use in surgical procedures such as cauterizing, cutting and similar procedures. Electrosurgical device 152 introduces RF cauterizing current, cutting current, or a blend thereof to an electrode 154 protruding from a nose area 156 of a longitudinal housing 158 by means of a finger-operated switch actuating member 160 disposed on housing 158.

Elastomeric seal 150 includes an elongated body portion 162 having a first opening 164 at a distal end 166 to accommodate varying diameters of electrodes or blades connected to electrosurgical device 152. A second opening 168 is defined at a proximal end 170 for partially fitting elastomeric seal 150 over housing 158 of electrosurgical device 152 as shown in FIG. 15. Seal 150 includes an actuating member pocket 172 in proximity to second opening 168 for fitting actuating member 160 therein. Seal 150 further includes a lip portion 174 and an elastic wall 176 in nose area 156 having a thickness that is greater than the thickness of body portion 162, thus providing a more rigid structure, for allowing seal 150 to maintain electrode 154 in place while preventing fluids from entering nose area 156 as shown by FIGS. 16–17A.

As can be seen from FIG. 18A, the diameter "d" of elastic wall 176 of nose area 156 is less than the diameter "D" of elongated body portion 162. The diameter "$d_1$" of lip portion 174 is less than the outer diameter of electrode 154 for seal 150 to further adhere to electrosurgical device 152 and prevent the ingress of contaminants. Lip portion 174 and elastic wall 176 also allow the accommodation of varying diameters of electrodes. Although the diameter "$d_1$" of lip portion 174 is shown to be less than the diameter "d" of elastic wall 176, it is also contemplated that they can be the same diameter.

After use, seal 150 can be resterilized or disposed of. Elastomeric seal 150 can be sterilized by accepted sterilization techniques such as, for example, autoclaving or EtO.

It is contemplated that seal 150 can be custom-molded for a particular electrosurgical device. It is further contemplated that seal 150 covers the entire housing 158 of electrosurgical device 152. Further still, it is contemplated that seal 150 fits snugly around housing 158 to a minimum of 32 mm beyond the closest active contact point of actuating member 160.

Figure 19:
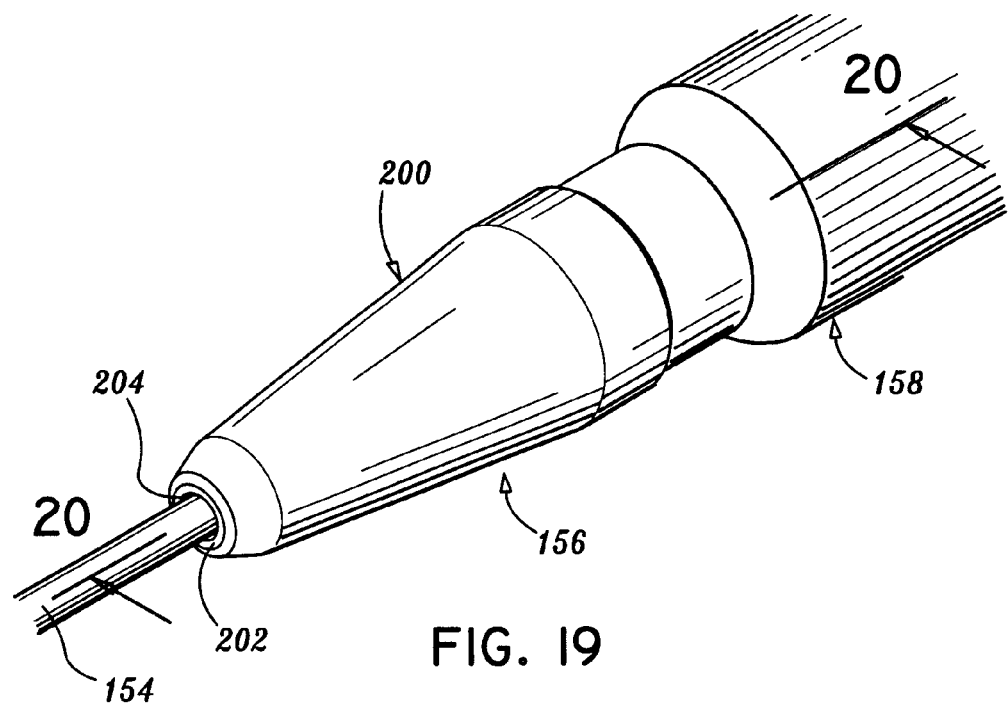
FIG. 19 is a perspective view of the nose area of an electrosurgical device having an elastomeric seal according to a second embodiment adhered thereto.
Figure 20:
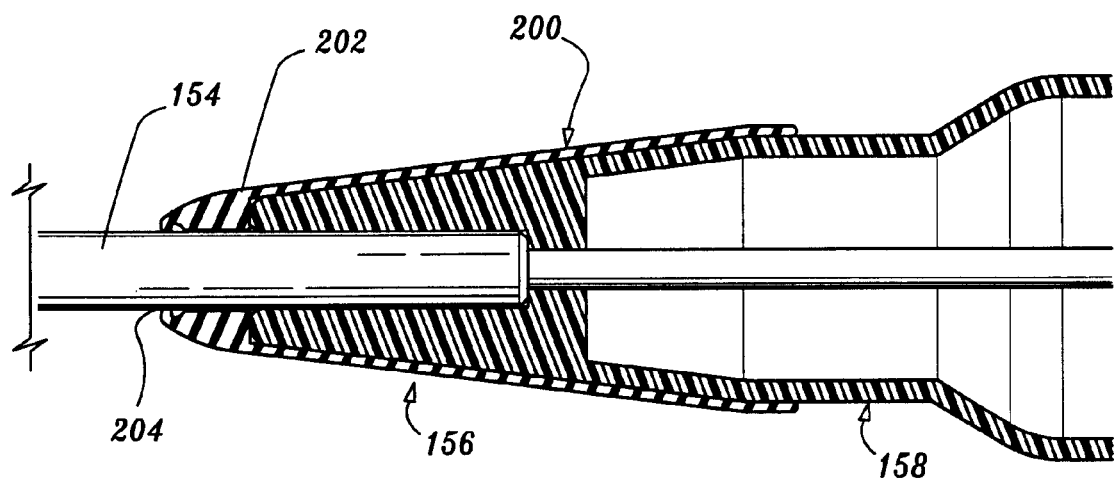
FIG. 20 is an enlarged, cross-sectional view taken along line 20—20 in FIG. 19.

With reference to FIGS. 19 and 20 there is shown an elastomeric seal of a second embodiment designated by reference numeral 200 and attached to nose area 156 of electrosurgical device 152. Seal 200 is chemically adhered to the nose area 156 which allows for seal 200 to be reusable. It is also contemplated that seal 200 can be mechanically attached to nose area 156 by rivets or other type of mechanical structure for allowing seal 200 to be disposable. It is further contemplated that seal 200 can be friction fit to nose area 156 of the electrosurgical device as well. Elastomeric seal 200 includes a soft lip 202 and an opening 204, as in the embodiment of FIGS. 14–18, to permit electrodes and blades of varying diameters to be inserted and sealed as shown by FIG. 20.

It is contemplated that seal 200 can be custom-molded for a particular electrosurgical device. Seal 200 is preferably manufactured from shore A durometer silicone or a thermoplastic elastomer. Seal 200 can be sterilized by accepted sterilization techniques such as, for example, autoclaving or EtO. After use, seal 200 can be resterilized or disposed of.

It will be understood that various modifications may be made to the embodiments disclosed herein. The above description should not be construed as limiting, but merely as exemplifications of preferred embodiments. Those skilled in the art will envision other modifications within the scope and spirit of the claims appended hereto.

What is claimed is:

1. An elastomeric seal for inhibiting the ingress of biomaterials into an electrosurgical device of the type having an electrode protruding from a distal end of a longitudinal housing for introducing current to said electrode for cauterizing or cutting body tissue, the elastomeric seal comprising:

an elongated body portion contoured for fitting upon said electrosurgical device, said elongated body portion further defining a first opening at a distal end and a second opening at a proximal end for fitting the elastomeric seal over the housing of said electrosurgical device, said elastomeric seal further defining an actuating member pocket for fitting an actuating member of the electrosurgical device therein; and a lip portion circumferentially surrounding said first opening.

2. The elastomeric seal according to claim 1, wherein said elastomeric seal is manufactured from shore A durometer silicone.

3. The elastomeric seal according to claim 1, wherein said elastomeric seal is manufactured from a thermoplastic elastomer.

4. The elastomeric seal according to claim 1, wherein said lip portion is configured to accommodate varying diameters of electrodes connected to said electrosurgical device.

5. The elastomeric seal according to claim 1, wherein said lip portion has greater elasticity than the body portion.

6. The elastomeric seal according to claim 1, wherein said elongated body portion has a uniform thickness.

7. The elastomeric seal according to claim 1, wherein a nose portion at the distal end of the seal has a greater thickness than said body portion.

8. The elastomeric seal according to claim 7, wherein the nose portion has an internal diameter less than the internal diameter of the body portion.

9. The elastomeric seal according to claim 8, wherein the lip portion has an internal diameter less than the internal diameter of the nose portion.

* * * * *

UNITED STATES PATENT AND TRADEMARK OFFICE
CERTIFICATE OF CORRECTION

PATENT NO. : 6,755,825 B2
DATED : June 29, 2004
INVENTOR(S) : Shoenman et al.

It is certified that error appears in the above-identified patent and that said Letters Patent is hereby corrected as shown below:

<u>Title page,</u>
Item [63], Related U.S. Application Data, insert:
-- Provisional application No. 60/101,489 filed on Sep. 23, 1998 --

Signed and Sealed this

Second Day of August, 2005

JON W. DUDAS
*Director of the United States Patent and Trademark Office*